United States Patent [19]

Falk

[11] 4,069,717
[45] Jan. 24, 1978

[54] MOLTEN METAL STREAM SAMPLER AND CLAMP

[76] Inventor: Richard A. Falk, 519 Westminster Drive, Waukesha, Wis. 53186

[21] Appl. No.: 739,217

[22] Filed: Nov. 5, 1976

[51] Int. Cl.$^2$ ............................................. G01N 1/12
[52] U.S. Cl. ............................................. 73/425.4 R
[58] Field of Search .................. 73/425.4 R, DIG. 9; 16/114 R, 114 A; 249/139; 294/27 R, 27 H, 33

[56] References Cited

U.S. PATENT DOCUMENTS

| | | | |
|---|---|---|---|
| 1,332,046 | 2/1920 | Kempton | 249/139 |
| 3,859,857 | 1/1975 | Falk | 73/DIG. 9 |
| 3,861,733 | 1/1965 | Mey | 294/33 |
| 3,994,172 | 11/1976 | Kelsey | 73/DIG. 9 |

*Primary Examiner*—S. Clement Swisher

*Attorney, Agent, or Firm*—Henry C. Fuller

[57] ABSTRACT

A sampler for taking a sample of molten metal from a stream of molten metal includes a mold body which is formed from two refractory mold halves with each half having an open faced cavity. In use the mold halves are secured together by spring clips which also press metal plates against the open mold faces to seal the open faces of the mold cavity. Grooves in the mold halves receive pin sample tubes and fill tubes. The split line between the mold halves affords venting of the mold cavity as the molten metal enters the mold cavity. The sample mold is manipulated by a handle which includes spring jaws with projections which are received in recesses in the mold halves. The spring jaws are expanded to receive and release the mold body by a lever arm secured to one of the jaws and extending along the handle.

3 Claims, 4 Drawing Figures

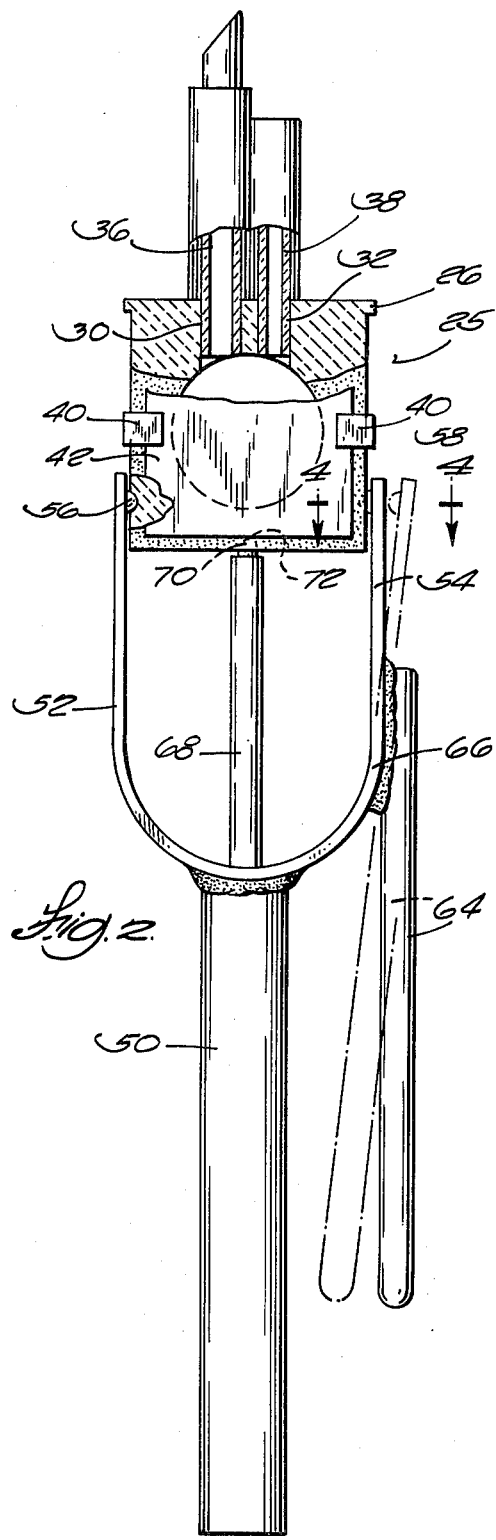
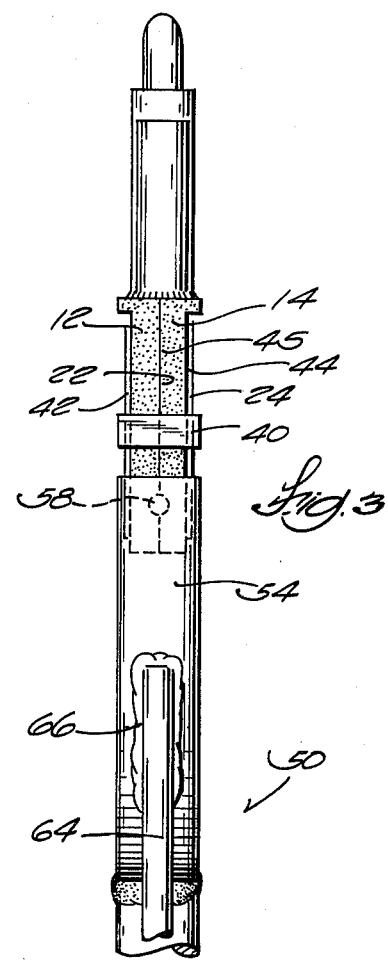
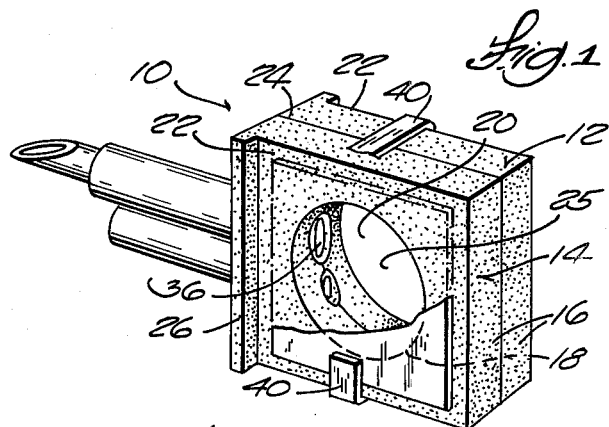
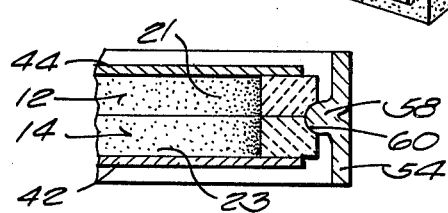

MOLTEN METAL STREAM SAMPLER AND CLAMP

SUMMARY OF INVENTION

The invention provides a molten metal sampler which is adapted for taking a sample from a stream of molten metal. The mold body is formed from two refractory mold halves which have flat interior and exterior surfaces with through openings. When the mold halves are held together by spring clips the split line between the mold halves provides a vent for release of air from the mold cavity during the metal filling process. The open faces of the mold are closed by steel plates pressed against the exterior surfaces of the mold halves by the spring clips. The spring clips will also provide a gripping action of the mold halves on fill tubes and pin sample tubes which extend through grooves in the mold halves for communication with the mold cavity.

A handle is provided with spring jaws having inwardly extending projections which are received in recesses in the mold body. A lever arm connected to one of the jaws and extending along the handle is easily gripped by the user to expand the jaws for insertion of the mold body prior to use and release of the mold body and sample subsequent to use.

Further objects and advantages of the invention will become apparent from the disclosure.

DESCRIPTION OF DRAWINGS

FIG. 1 is a perspective view of a sampler in accordance with the invention.

FIG. 2 is a view of a sampler and a handle in accordance with the invention.

FIG. 3 is an end view of the sampler shown in FIG. 2.

FIG. 4 is a sectional view along line 4—4 of FIG. 2.

DESCRIPTION OF PREFERRED EMBODIMENT

In the drawings, FIG. 1 discloses a mold body 10 formed from first and second mold halves 12 and 14. Each mold half 12 and 14 has a peripheral body wall 16 which surrounds and defines a central open faced cavity 18. When the mold halves are assembled to form a mold body 25 the open cavities are aligned to form a mold cavity 20 with openings 21, 23.

The mold halves 12 and 14 have flat interior and exterior surfaces 22 and 24. Each mold half can also include an outwardly extending lip 26 to provide a metal splash shield.

Each mold half 12 and 14 is provided with a recess 30 for a fill tube and a recess 32 for a pin sample tube. When the mold halves are assembled together as presently described the recesses register to provide through openings from the exterior of the mold body to the mold cavity 20 to grip a fused quartz fill tube 36 and a pin sample tube 38.

Means are provided for enclosing the open faces of the mold and for clamping the mold halves together. In the disclosed construction the means comprises metal spring clips 40 which are generally u-shaped and arranged around the mold halves. The closure means is in the form of steel plates 42 and 44 which are compressed against the flat exterior surfaces by the clips 40 to cover the openings. When the mold halves 12, 14 are assembled and held together by the clips 40, the split line 45 between the mold halves serves as a vent for exhausting air from the mold cavity when metal flows into the cavity.

A handle is provided for manipulating the sample mold in use. As disclosed the handle 50 includes opposed spring jaws 52 and 54 with projections 56 and 58 which register with recesses 60 in each mold half which recesses together, form anular depressions. A lever arm 64 is provided for expanding one of the jaws 54 for insertion and release of a sample body. Lever arm 64 is welded at 66 to a jaw 54 and extends along the handle 50. The lever arm 64 is easily manually gripped by the user and depressed to the broken line position shown in FIG. 2 to expand the jaws. The handle also includes an axially extending rod 68 with a tip 70 which extends into a recess 72. The rod 68 prevents pivotal motion or displacement of the mold body 25 about the axis resulting from the connection of the projections 56 and 58 and the recesses 60 in the mold body.

I claim:

1. A sampler for taking a sample of molten metal comprising a pair of mold halves, each of said mold halves having wall means defining a peripheral boundary wall for an open faced cavity, said boundary wall having flat interior and exterior surfaces, grooves extending from the outer margin of the boundary wall to the cavity, a fill tube, and closure means for enclosing said open faces, and means for clamping said closure means against said exterior faces and said mold halves together with said grooves in registry and in clamping engagement with a portion of said fill tube with the split line between said mold halves providing an air vent.

2. A sampler in accordance with claim 1 wherein said closure means comprises metal plates and said clamping means comprises generally u-shaped spring clips which extend inwardly over said boundary wall and embrace the plates and urge the plates against the exterior flat surfaces of the mold halves.

3. A sampler for taking a sample of molten metal comprising a mold body having spaced walls with first and second recesses, a handle having jaws spaced to receive the mold body therebetween, projections on said jaws registrable with the recesses in said mold body and means for expanding the gap between said jaws to receive said mold body, and wherein said jaws have diverging portions which diverge from a common juncture with a pipe and said means to expand the gap between the jaws comprises a manual lever connected to one of said jaws and extending along the handle and including a third recess on said body offset from said first and second recesses and means on said handle registrable with said third recess to prevent displacement of said mold body about the first and second recesses.

* * * * *